(12) United States Patent
Rustenbeck et al.

(10) Patent No.: US 9,107,846 B2
(45) Date of Patent: Aug. 18, 2015

(54) FORMULATION

(75) Inventors: Peter Rustenbeck, Herrenberg (DE); Martina Schmid, Herrenburg (DE); Christoph Theurer, Herrenberg (DE); Stephan Wurtz, Herrenberg (DE)

(73) Assignee: Omega Pharma Innovation and Development NV, Nazareth (BE)

( * ) Notice: Subject to any disclaimer, the term of this patent is extended or adjusted under 35 U.S.C. 154(b) by 1275 days.

(21) Appl. No.: 12/666,609

(22) PCT Filed: Jul. 2, 2008

(86) PCT No.: PCT/EP2008/058530
§ 371 (c)(1),
(2), (4) Date: Dec. 23, 2009

(87) PCT Pub. No.: WO2009/004039
PCT Pub. Date: Jan. 8, 2009

(65) Prior Publication Data
US 2010/0183709 A1     Jul. 22, 2010

(30) Foreign Application Priority Data

Jul. 4, 2007  (GB) .................................. 0712972.9

(51) Int. Cl.
*A61K 36/42* (2006.01)
*A61K 9/48* (2006.01)
*A61K 36/185* (2006.01)
*A61K 36/22* (2006.01)
*A61K 36/48* (2006.01)

(52) U.S. Cl.
CPC ............. *A61K 9/4858* (2013.01); *A61K 36/185* (2013.01); *A61K 36/22* (2013.01); *A61K 36/42* (2013.01); *A61K 36/48* (2013.01)

(58) Field of Classification Search
None
See application file for complete search history.

(56) References Cited

U.S. PATENT DOCUMENTS

| | | | | |
|---|---|---|---|---|
| 4,450,877 A | * | 5/1984 | Walker et al. | ...................... 141/1 |
| 5,565,214 A | * | 10/1996 | Zambo et al. | ................. 424/456 |
| 6,261,607 B1 | * | 7/2001 | Newmark et al. | ............. 424/727 |
| 2008/0031940 A1 | * | 2/2008 | Rodriguez | .................... 424/457 |

* cited by examiner

*Primary Examiner* — Chris R Tate
*Assistant Examiner* — Deborah Davis
(74) *Attorney, Agent, or Firm* — Crowell & Moring LLP

(57) ABSTRACT

The present invention relates to therapeutic formulations based on pumpkin products, in particular to encapsulated formulations for oral administration. A product of the invention comprises a hard gelatin capsule which encloses a unit dose of a formulation which comprises at least 50% by weight of one or more pumpkin product.

17 Claims, 1 Drawing Sheet

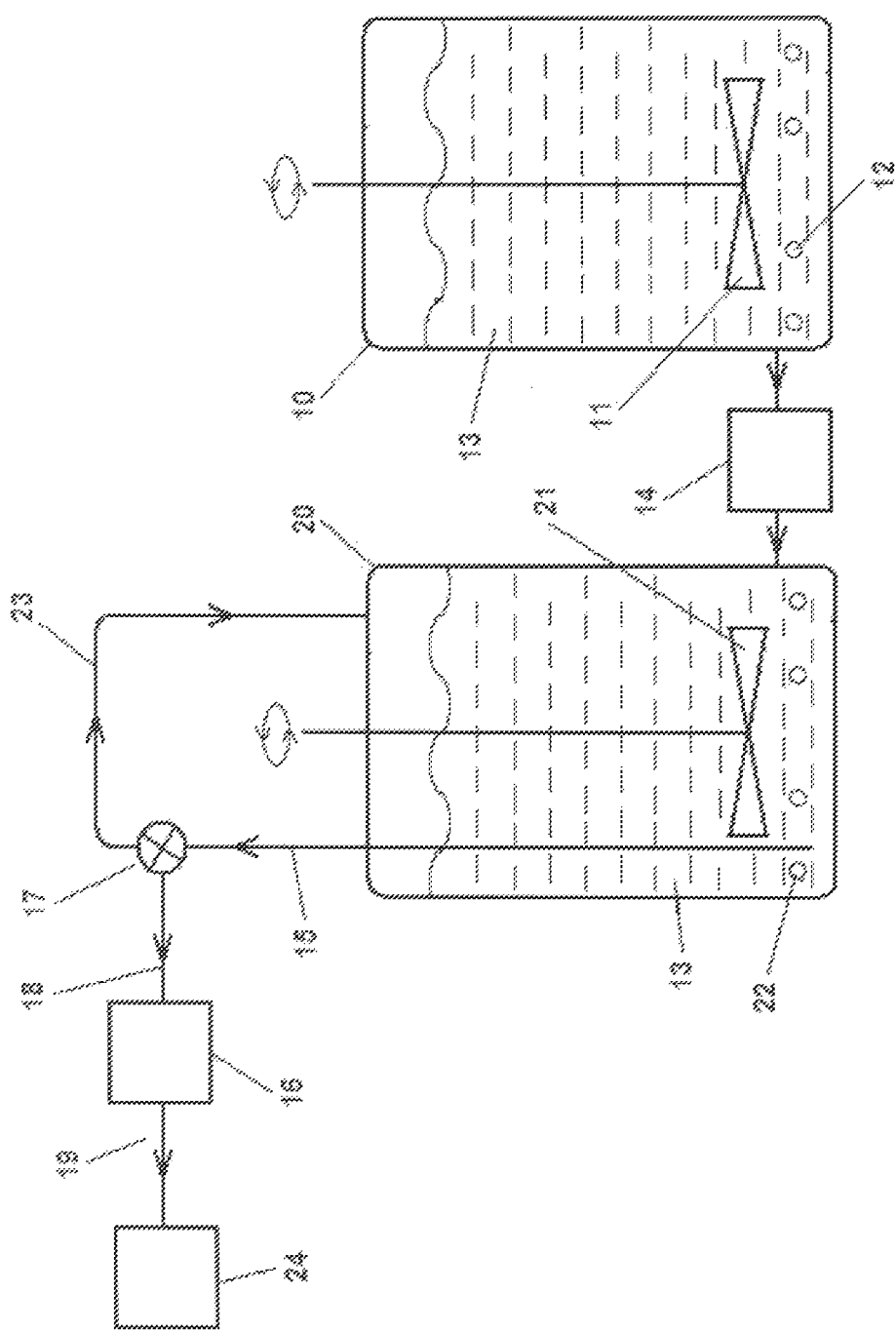

FORMULATION

This application is a §371 national phase entry of International Application No. PCT/EP2008/058350, filed Jul. 2, 2008.

This invention relates to therapeutic formulations based on pumpkin products, in particular to encapsulated formulations for oral administration.

The pumpkin is a squash fruit, usually orange in colour when ripe (though there may be white, red and grey varieties). Pumpkins grow as a gourd from trailing vines of the genus *Curcurbita* (family Curcurbitaceae). *Curcurbita* species include *Curcurbita pepo, Curcurbita maximo, Curcurbita mixta* and *Curcurbita moschata*. The pumpkin varies in form, being sometimes oblate spherical, but more generally oblong or ovoid in shape. The common pumpkin is known as the "Giant" variety. The term "pumpkin" as used herein includes all members of the pumpkin family. Pumpkins are both edible as a food, and useful as a therapeutic product. Pumpkin seeds are a good source of iron, zinc, essential fatty acids, potassium and magnesium. Pumpkin seeds are believed to promote prostate health as components of pumpkin seed oil appear to interrupt the triggering of prostate cell multiplication by testosterone and DHT. Pumpkin seed oil is also believed to be helpful in prevention of inflamed bladder syndrome. The term "pumpkin product" as used herein refers to any product derived from pumpkin, for example pumpkin seed oil, pumpkin seed, or mixtures thereof.

Pumpkin products are commonly formulated into therapeutic products together with other so-called natural products such as plant extracts etc.

It is well known to provide pumpkin seeds and pumpkin seed oil for oral administration encapsulated in gelatin capsules. Gelatin capsules may be either soft or hard. To date soft gelatin capsules have been used with pumpkin products such as seeds and oil. For example U.S. Pat. No. 5,565,214 discloses the encapsulation of pumpkin seed oil in soft gelatin capsules. There are many other disclosures of pumpkin healthcare products.

There is a difference in the manufacturing processes used for soft and hard gelatin capsules. With soft gelatin capsules the content to be encapsulated is enclosed between half-capsule shells as the soft capsule is formed. With hard gelatin capsules the hard gelatin part shells are first made, the content is filled into one part shell, the second part capsule shell is fitted in a telescoping manner over the first, filled, part shell, and the two shells are adhered together, typically by applying water or aqueous ethanol to the interface between the two shells to create a bond between the two part shells. Hard gelatin capsules are preferred because they can more easily be used in blister packs with less risk of bursting the capsule when it is forced out through the foil of the blister.

There are problems associated with the encapsulation of pumpkin products such as oil, seed, or mixtures thereof, particularly into hard gelatin capsules. This problem arises from the fibrous content of pumpkin products. Fibres tend to become trapped between the capsule shells and prevent complete bonding between the capsule shells. This can result in subsequent leakage of content.

There is a further problem associated with pumpkin products, particularly pumpkin products based on a mixture of particles of pumpkin seeds and pumpkin seed oil, in that the particulate content tends to separate out and settle to the bottom of any containing vessel. For this reason such pumpkin products are normally formulated with excipients, some of which may help reduce settling, particularly emulsifying excipients such as beeswax or soya oil. The need for such excipients reduces the fill weight of the useful pumpkin ingredients.

It is an object of the present intention to address such problems of pumpkin products, by providing a novel pumpkin product, a novel process for encapsulating pumpkin products, and an apparatus for performing this process.

According to a first aspect of this invention, a product is provided comprising a hard gelatin capsule which encloses a unit dose of a formulation which comprises at least 50% by weight of one or more pumpkin product.

Typically a hard gelatin capsule is of the type comprising two part capsule shells, one of which is first filled with the formulation, then the other of which is connected thereto to close the capsule. Typically the two part capsule shells can be connected together by a solvent weld of known type, e.g. using water or aqueous ethanol.

Preferably the formulation comprises at least 80% by weight of one or more pumpkin product, more preferably at least 90% by weight of one or more pumpkin product, more preferably still at least 95% by weight of one or more pumpkin product. Most preferably the formulation comprises 100% by weight of one or more pumpkin product, i.e. being free of excipients. The invention therefore facilitates a capsule that encloses a formulation that comprises entirely one or more pumpkin product.

Suitably the formulation may comprise pumpkin seed or pumpkin seed oil or a mixture thereof. Such a formulation may suitably consist entirely of pumpkin seed or pumpkin seed oil or a mixture thereof.

One or more other non-pumpkin ingredient may be included in the formulation, for example one or more other healthcare product such as one or more herbal extract and/or soya oil, one or more vitamin such as Vitamin E (tocopherol acetate), one or more surfactant such as Lecithin, and other common excipients such as beeswax, glycerol etc. Many such ingredients are traditional in pumpkin product formulations.

Suitably a mixture of pumpkin seed:pumpkin seed oil, whether or not any additional healthcare product is present in the formulation, may be in a weight ratio range 60:40-40:60.

A first suitable formulation of this invention is a mixture of pumpkin seed oil and particulate pumpkin seeds comprising a weight ratio 40-50 pumpkin seed oil:60-50 particulate pumpkin seed, this mixture forming 100% of the formulation.

A second suitable formulation of this invention is a mixture of 75-85 weight % pumpkin product being the above-mentioned mixture of pumpkin seed oil and particulate pumpkin seeds comprising a weight ratio 40-50 pumpkin seed oil:60-50 particulate pumpkin seed, together with 25-15 weight % of a vegetable extract or a herbal extract, such as a dried extract of saw palmetto, totaling 100 weight %.

A third suitable formulation of this invention is a mixture of 50-60 weight % of pumpkin seed oil, together with 15-20 weight % sweet sumach bark extract, 4-5 weight % extract of hops, 5-15 weight % of soya oil, 3-10 weight % of an emulsifying wax such as beeswax, and 3-7 weight % of one or more vitamin, totaling 100 weight %.

In the formulation the pumpkin seed, and preferably also any other particulate material such as other pumpkin residues, are preferably in a particle size of less than 300 microns, more preferably less than 200 microns. This small particle size may be beneficial in minimising the above-mentioned problem of leakage from capsules. Such a particle size may be achieved by for example a colloid mill.

In a second aspect the present invention further provides a process for the encapsulation of pumpkin products which addresses the encapsulation of pumpkin products with their associated problem of their fibrous content hindering leak-proof sealing of hard gelatin capsules.

Accordingly, a process for the encapsulation of pumpkin products in hard gelatin capsules is provided, wherein:

a liquid formulation comprising pumpkin seed oil is provided in a vessel, the liquid formulation in the vessel is agitated so as to maintain any particulate matter therein in suspension, whilst the liquid formulation within the vessel is agitated the formulation is fed to a capsule filling station via a filling flow line, a unit dose volume of the liquid formulation is introduced into hard gelatin part capsules via the capsule filling station, excess liquid formulation which has not been introduced into the hard gelatin part capsule at the capsule filling station is returned back to the vessel, so that whilst liquid formulation is introduced into the hard gelatin part capsule, the formulation is circulated between the vessel and the capsule filling station, then the part capsules are closed to form a closed capsule after introduction of the formulation into the part capsules.

It is found that by agitating the formulation in the vessel, and by circulating the formulation between the vessel and the filling station particulate matter in the formulation, e.g. particulate pumpkin matter, can be maintained in suspension without the need for suspending agents. This can facilitate the filling of the hard gelatin capsules with a formulation which consists entirely of pumpkin products, i.e. being excipient-free.

Suitable and preferred examples of formulations comprising pumpkin seed oil are described above in connection with the first aspect of this invention.

Preferably the formulation comprises a mixture of pumpkin seed oil and particulate pumpkin seeds.

The liquid formulation in the vessel is suitably agitated by a generally conventional stirrer.

Preferably prior to introducing the formulation into the hard gelatin part capsule the particle size of any particulate matter is reduced to a particle size of less than 300 microns, more preferably less than 200 microns. Such a particle size may be achieved by for example passing the formulation through a mill, suitably a corundum disc colloid mill. Suitably, especially in the case of the pumpkin products mentioned above wherein the formulation comprises a mixture of pumpkin seed:pumpkin seed oil may in a weight ratio range 60:40-40:60, the formulation comprising 50% to 100% by weight of such a mixture, this particle size reduction is performed at a temperature of 80-100° C., for example 90-95° C. This elevated temperature may assist size reduction by reducing the viscosity of the formulation.

When the formulation is to contain one or more other healthcare product such as one or more vegetable extract and/or herbal extract and/or soya oil, one or more vitamin such as Vitamin E (tocopherol acetate), one or more surfactant such as Lecithin, and/or one or more other common excipient such as beeswax, glycerol etc. such one or more product may be added into the formulation before or preferably after the above-mentioned particle size reduction. For example such substances may be added into the formulation with the formulation at a temperature of 40-75° C.

The formulation may then be adjusted if necessary to a suitable temperature for filling into the part capsule (part capsule shell). A suitable temperature, particularly with the pumpkin products mentioned above comprising a mixture of pumpkin seed:pumpkin seed oil in a weight ratio range 60:40-40:60, such a formulation comprising 50% to 100% by weight of such a mixture, is around 40+/−5° C. At such a temperature the above-mentioned formulations are found to have a viscosity convenient for filling into hard gelatin capsules.

After the formulation has been filled into the part capsule, this may be closed in a generally conventional manner by connecting another part capsule in a telescoping manner.

Thereafter the closed capsule may be sealed in a generally conventional manner by for example the application of water or a water:solvent e.g. water:ethanol mixture to the junction region between the two part capsules. Preferably if the formulation has been introduced into the part capsule at a temperature above ambient temperature then the closed capsule should be cooled to ambient temperature, and the sealing operation performed with the closed capsule at around ambient temperature. This cooling may be achieved using a conventional cooling conveyor on which the closed capsules are transported under a flow of cold air.

The process is preferably performed under GMP conditions and a level of sterility which is appropriate for an orally administered healthcare product.

The invention further provides an apparatus configured to perform the process of this invention, comprising:

a vessel of a suitable capacity to contain a bulk volume of liquid formulation, and provided with a stirrer whereby the liquid formulation in the vessel may be agitated so as to maintain any particulate matter therein in suspension, a capsule filling station, the vessel being in communication with the capsule filling machine via a filling flow line whereby the formulation may be fed to the capsule filling station, a branch from the filling flow line leading from the filling flow line to the capsule filling station, and a return flow line via which excess formulation which is not taken up by the capsule filling station is fed back to the vessel to thereby maintain continuous agitation and circulation of the formulation.

Parts of this apparatus may be otherwise conventional, and may be made of conventional materials. Parts which come into contact with the formulation may, for example, be made of stainless steel.

The invention will now be described by way of example only with reference to the accompanying drawing, FIG. 1 which shows schematically an apparatus for performing the process of this invention to prepare a product of the invention.

Features identified in FIG. 1 are listed below.

10 first stainless steel tank
20 second stainless steel tank
11,21 stirrers
12, 22 heaters
13 pumpkin product formulation
14 colloid mill
15 stainless steel flow line
16 capsule filling machine
17 valve
18 branch of the flow line
19 conveyor
23 return flow line
24 capsule sealing machine.

Referring to FIG. 1 an apparatus is shown schematically. The apparatus comprises first and second stainless steel tanks respectively 10,20 each of a suitable capacity to contain the bulk volume of formulation to be used. The tanks 10,20 are each provided with respective conventional stirrers 11,21 and heaters 12,22.

A suitable working volume of pumpkin product formulation 13 e.g. a mixture of pumpkin oil and pumpkin seed, is introduced into the first tank 10. The mixture is heated by means of the heater 12, and the mixture is stirred. The formulation 13 is pumped out of tank 10 by means of a suitable pump (not shown) and is passed through colloid mill 14 to reduce the particle size of the pumpkin seed component. From colloid mill 14 the milled formulation 13 is fed into second tank 20 and is maintained stirred and at a suitable temperature therein.

Other ingredients such as the various extracts etc. mentioned herein may be added to the composition 13 in tank 10 or 20 and mixed in at suitable stages by thorough stirring using stirrer 11, 21.

The formulation 13 in tank 20 is then allowed to cool in a conventional manner, e.g. by the use of a cooler, or flowing cold water through the coils of a hot water or steam heater 22 whilst maintaining stirring.

When the formulation 13 is at a suitable temperature for filling hard shell gelatin capsules the formulation is fed via flow line 15 to a capsule filling machine 16. In practice an unmodified Bosch GKF 1400 L machine was used. The machine 16 was fed via valve 17 opening from flow line 15 into branch 18 of the flow line 15, and excess formulation which is not taken up by the machine 16 is fed back via flow line 23 to the tank 20 to thereby maintain continuous stirring and circulation of the formulation 13.

The operation of the machine 16 is conventional, i.e. a unit dose volume of the formulation 13 is introduced into a part capsule shell of a hard gelatin capsule (not shown), and the capsule shell containing the formulation is then closed with a second capsule shell (not shown) in a conventional manner. In the process of the invention the capsules (not shown) are at an elevated temperature, above that conventionally used in capsule sealing. The closed capsules (not shown) are now sent along cooling conveyor 19 during which a downward flow of cold air is directed upon them. The cooled capsules (not shown) are fed by the conveyor 19 to a capsule sealing machine 24. In practice a Lems 30 or Lems 60 machine was used. In this machine 24 the closed capsules were sealed in a conventional manner by means of spraying the interface between the two part capsule shells with a 50:50 ethanol:water mixture.

The sealed capsules are then subjected to standard quality control procedures such as leak testing by exposure to reduced atmospheric pressure, visual inspection etc. before packaging e.g. in conventional blister packs.

Pumpkin Product Formulations.

Three pumpkin product formulations of this invention are now described, which can be encapsulated using the apparatus and process described above.

Product 1.

| Ingredient | Weight % | Kg per 800 Kg |
|---|---|---|
| Pumpkin seeds | 54.054 | 432.4 |
| Pumpkin seed oil | 45.946 | 367.6 |
| Total | 100% | 800 Kg |
| Hard gelatin capsules. Licaps Gr. 00, red-brown opaque. | | 1,081,081 |
| i) Sealing liquid. Not contained in final product. | | |
| Ethanol (96%) Ph. Eur | — | 25 Kg |
| Purified Water Ph. Eur | — | 25 Kg |
| ii) Alternative quantities for sealing liquid components. Not contained in final product. | | |
| Ethanol (96%) Ph. Eur | — | 35 Kg |
| Purified Water Ph. Eur | — | 35 Kg | a) Production of Bulk Mixture

An 800 kg batch of pumpkin seeds and pumpkin seed oil was introduced into a stainless steel tank 10 as above, and the mixture was heated to 90-95° C. and maintained at this temperature for 30 minutes. The particle size of particulate pumpkin matter was then reduced to <200 micron by passage through a colloid mill 14 as above. Then the mixture in the tank 20 was cooled to 40° C. This mixture was maintained under constant stirring.

b) Capsule Filling

The mixture was fed at this temperature of 40° C. to the Bosch GKF 1400 L capsule filling machine 16, and was filled into hard gelatin capsules as described above. The filled hard gelatin capsules were then cooled to ambient temperature using the cooling conveyor 19 as described above, and then sealed using the Capsugel LEMS 60 capsule filling machine 24 and loaded onto trays.

c) Testing of Capsules; Storing of Capsules

After one hour the sealed capsules in their trays were put in a vacuum chamber (20 minutes suction at 250 mbar and 10 minutes standing time). After at least four hours standing time the trays were optically checked for leaks, and leaking capsules were manually removed. After this the capsules were stored in plastic sacks for sealing into blister packs. It was found that the constant stirring and circulation enabled the mixture to remain as a suspension of pumpkin particulates without the need for excipients.

Product 2a.

| Ingredient | Weight % | Kg per 250 Kg |
|---|---|---|
| Mixture of pumpkin seeds and pumpkin seed oil as used in Product 1 | 79.78 | 199.46 |
| Dried extract of saw palmetto fruit (4:1, extraction medium 90% ethanol) | 20.22 | 50.54 |
| Total | 100% | 250 Kg |

A 250 kg batch of pumpkin seeds and pumpkin seed oil was introduced into a stainless steel tank as above, and the mixture was heated to 90-95° C. and maintained at this temperature for 30 minutes. The particle size of particulate pumpkin matter was then reduced to <200 micron. Then the mixture was cooled to 50° C. To this mixture was added the dried extract of saw palmetto fruit. After the mixing the mixture was homogenized to reduce the size of any agglomerates. This mixture was maintained under constant stirring. The mixture was cooled to 40° C. and fed at this temperature to the Bosch GKF 1400 L capsule filling machine, and was filled into hard gelatin capsules as described above. The filled hard gelatin capsules were then cooled to ambient temperature using the cooling conveyor as described above, and then sealed using the Capsugel LEMS 60 capsule filling machine and loaded onto trays. After one hour the sealed capsules in their trays were put in a vacuum chamber (20 minutes suction at 250 mbar and 10 minutes standing time). After at least four hours standing time the trays were optically checked for leaks, and leaking capsules were manually removed. After this the capsules were stored in plastic sacks for sealing into blister packs. It was found that the constant stirring and circulation enabled the mixture to remain as a suspension of pumpkin particulates without the need for excipients.

Product 2b.

| Ingredient | Weight % | Kg per 800 Kg |
|---|---|---|
| Pumpkin seeds | 43.13 | 320.0 |
| Pumpkin seed oil | 36.66 | 272.0 |
| Dried extract of saw palmetto fruit (4:1, extraction medium 90% ethanol) | 20.22 | 150.0 |
| Total | 100% | 800.0 Kg |
| Hard gelatin capsules. Licaps Gr. 00, elongated brown opaque. | | 800.000 |
| Sealing liquid. Not contained in final product. | | |
| Ethanol (96%) Ph. Eur | — | 35 Kg |
| Purified Water Ph. Eur | — | 35 Kg | a) Production of Bulk Mixture

An 800 kg batch of pumpkin seeds and pumpkin seed oil was introduced into a stainless steel tank 10 as above, and the mixture was heated to 90-95° C. The particle size of particulate pumpkin matter was then reduced to <200 micron by passage through a colloid mill 14 as above. Then the mixture in the tank 20 was cooled to 50° C. This mixture was maintained under constant stirring.

To this mixture was added the dried extract of saw palmetto fruit. After the mixing the mixture was homogenized to reduce the size of any agglomerates.

The mixture was then cooled to 40° C. This mixture was maintained under constant stirring.

b) Capsule Filling

The mixture was fed at this temperature of 40° C. to the Bosch GKF 1400 L capsule filling machine 16, and was filled into hard gelatin capsules as described above. The filled hard gelatin capsules were then cooled to ambient temperature using the cooling conveyor 19 as described above, and then sealed using the Capsugel LEMS 60 capsule filling machine 24 and loaded onto trays.

c) Testing of Capsules; Storing of Capsules

After one hour the sealed capsules in their trays were put in a vacuum chamber (20 minutes suction at 250 mbar and 10 minutes standing time). After at least four hours standing time the trays were optically checked for leaks, and leaking capsules were manually removed. After this the capsules were stored in plastic sacks for sealing into blister packs. It was found that the constant stirring and circulation enabled the mixture to remain as a suspension of pumpkin particulates without the need for excipients.

Product 3.

| Ingredient | Weight % | Kg per 250 Kg |
|---|---|---|
| Pumpkin seed oil | 50.512 | 126.28 |
| Dried extract of sweet sumach bark extract (70% native extract, DEV 5-7:1) | 17.776 | 44.44 |
| Dried extract of hops (90% native extract, DEV 5.5-6.5:1) | 4.444 | 11.11 |
| Soya oil, partially hydrogenated DAB | 10.444 | 26.11 |
| Wax, yellow Ph Eur | 6.668 | 16.67 |
| Tocopherol acetate, dl alpha Ph. Eur | 4.668 | 11.67 |
| Lecithin, Soya lecithin with 60% Phosphatide NF USP | 3.932 | 9.83 |
| Glycerol 85% Ph. Eur | 1.556 | 3.89 |
| Total | 100% | 250 Kg |
| Hard gelatin capsules. Licaps Gr. 0, red-brown opaque. | | 555,555 |

| Ingredient | Weight % | Kg per 250 Kg |
|---|---|---|
| Sealing liquid. Not contained in final product. | | |
| Ethanol (96%) Ph. Eur | — | 25 Kg |
| Purified Water Ph. Eur | — | 25 Kg |

Yellow wax, soya oil and pumpkin seed oil were introduced into the tank and heated to 70° C. until all liquid. After cooling, to this mixture was added sequentially the Lecithin, Glycerol and Tocopherolacetate. After this mixing the dried extract of hops, and the sweet sumach bark extract were added and mixed in. Then the mixture was homogenised to remove any agglomerates. After the homogenization the bulk mixture was de-aerated. The mixture was then encapsulated as described above under Products 1 and 2b, and the capsules checked for leaks as described above under Products 1 and 2b.

The invention claimed is:

1. A process for the production of a hard gelatin capsule encapsulating a formulation comprising at least 50% by weight of a pumpkin product comprising pumpkin seed oil and particulate pumpkin seed matter wherein the process comprises the steps of:
    providing a liquid formulation comprising pumpkin seed oil and particulate pumpkin seed matter in a vessel;
    agitating the liquid formulation so as to maintain the particulate pumpkin seed matter therein in suspension;
    feeding the formulation into a capsule filling station via a filling flow line;
    introducing a unit dose volume of the liquid formulation into a hard gelatin part capsule via the filling station whereby prior to introducing the formulation into the hard gelatin part capsule, wherein the particle size of the pumpkin seed matter is reduced to a particle size of less than 300 microns; and
    closing the hard gelatin part capsule to form a closed capsule after introduction of the formulation into the hard gelatin part capsule.

2. The process according to claim 1 wherein the particle size is reduced to a particle size of less than 200 microns.

3. The process according to claim 1 wherein the particle size is reduced at a temperature of 80-100° C.

4. The process according to claim 3 wherein the particle size is reduced at a temperature of 90-95° C.

5. The process according to claim 1 wherein one or more additional ingredients selected from the group consisting of herbal extracts, soya oil, vitamins and surfactants are added to the formulation after the particle size reduction.

6. The process according to claim 5 wherein the addition of the one or more additional ingredients is performed with the formulation at a temperature of 40-75° C.

7. The process according to claim 1 wherein the formulation is filled into the hard gelatin part capsule at a temperature of 40+/−5°πC.

8. The process according to claim 1 wherein the closed hard gelatin part capsule is maintained at, or cooled to ambient temperature as required, and sealed at around ambient temperature.

9. A hard gelatin capsule encapsulating a formulation comprising at least 50% of the pumpkin product produced by the method according to claim 1.

10. The hard gelatin capsule according to claim 9, wherein the formulation comprises at least 80% by weight of said pumpkin product.

11. The hard gelatin capsule according to claim 10, wherein the formulation comprises 100% by weight of said pumpkin product.

12. The hard gelatin capsule according to claim 9 wherein the formulation additionally comprises one or more ingredients selected from the group consisting of herbal extracts, soya oil, vitamins and surfactants.

13. The hard gelatin capsule according to claim 9 wherein the formulation comprises a weight ratio of the particulate pumpkin seed matter:pumpkin seed oil in a range of 60:40-40:60, respectively.

14. The hard gelatin capsule according to claim 13 wherein the formulation comprises a weight ratio of the pumpkin seed oil:particulate pumpkin seed matter in a range of 40-50:60-50, respectively, so as to provide 100% of the formulation.

15. The hard gelatin capsule according to claim 9 wherein the formulation further comprises 15-25 weight % of a vegetable extract or an herbal extract, totaling 100 weight %.

16. A hard gelatin capsule encapsulating a formulation, wherein the formulation comprises a mixture of 50-60 weight % of pumpkin seed oil, 15-20 weight % sweet sumac bark extract, 4-5 weight % extract of hops, 5-15 weight % of soya oil, 3-10 weight % of an emulsifying wax, and 3-7 weight % of one or more vitamins, totaling 100 weight %.

17. The hard gelatin capsule according to claim 9, wherein the particle size of the particulate pumpkin seed matter is less than 200 microns.

\* \* \* \* \*